United States Patent [19]

Axen et al.

[11] E Re. 29,480

[45] Reissued Nov. 22, 1977

[54] METHOD FOR DETERMINING VITAMIN $B_{12}$ AND REAGENT THEREFOR

[75] Inventors: Rolf E. A. V. Axen, Upplands Balinge; Jerker O. Porath; Leif Edvin Wide, both of Uppsala, all of Sweden

[73] Assignee: Pharmacia AB, Uppsala, Sweden

[21] Appl. No.: 598,142

[22] Filed: July 23, 1975

Related U.S. Patent Documents

Reissue of:

[64] Patent No.: 3,505,019
Issued: Apr. 7, 1970
Appl. No.: 675,323
Filed: Oct. 16, 1967

[30] Foreign Application Priority Data

Oct. 21, 1966 Sweden ..... 14397/66

[51] Int. Cl.[2] ..... G01N 23/00; G01N 33/16; G01T 1/16

[52] U.S. Cl. ..... 424/1.5; 23/230 B; 23/230.6; 252/408

[58] Field of Search ..... 23/230 B, 230.3, 230.6; 424/1, 1.5

[56] References Cited

U.S. PATENT DOCUMENTS

| | | | |
|---|---|---|---|
| 3,555,143 | 1/1971 | Axen et al. | 23/230 B X |
| 3,646,346 | 2/1972 | Catt | 23/230 B X |

OTHER PUBLICATIONS

Axen et al., Nature, v. 210, pp. 367–369 (1966).
Axen et al., Chemical Abstracts, v. 62:11911e (1965).
Axen et al., Nature, v. 214, pp. 1302–1304 (1967).
Barakat et al., Lancet, v. ii, pp. 25–26 (1961).
Ceska et al., Clin. Chim. Acta, v. 32, pp. 339–354 (1971).
Bacher, F. A. et al., Analytical Chemistry, vol. 26, pp. 1146–1149 (1954).
Bunge, M. B. et al., Chemical Abstracts, vol. 52, p. 5570 (1958).
Shaw, W. H. C. et al., Analyst, vol. 85, pp. 389–409 (1960).

*Primary Examiner*—Sidney Marantz
*Attorney, Agent, or Firm*—Hubbell, Cohen, Stiefel & Gross

[57] ABSTRACT

Method for determining vitamin $B_{12}$ in aqueous samples by contacting said sample with radioactivity labelled vitamin $B_{12}$ and with particles of water insoluble polymers to which substances capable of binding vitamin $B_{12}$ have been bound, thereafter separating said particles and determining the radioactivity.

31 Claims, No Drawings

METHOD FOR DETERMINING VITAMIN $B_{12}$ AND REAGENT THEREFOR

Matter enclosed in heavy brackets [ ] appears in the original patent but forms no part of this reissue specification; matter printed in italics indicates the additions made by reissue.

The present invention relates to a method for determining vitamin $B_{12}$ in aqueous samples e.g. from body fluids such as blood serum, and a reagent to be used for the method.

The invention characterized in that particles of water-insoluble polymers to which a substance capable of binding vitamin $B_{12}$ has been bound by covalent bonds, are contacted with the sample fluid and with a certain quantity of vitamin $B_{12}$ labelled with a radioactive isotope, whereafter, subsequent to the reaction between vitamin $B_{12}$ and the substance capable of binding vitamin $B_{12}$ attached to the particles having taken place, the particles are separated from the sample fluid and the radioactivity of the particle material and/or in the fluid is determined.

The method can be utilized for qualitative and quantitative determination.

In the present instance the term "substance capable of binding vitamin $B_{12}$" is meant to signify a substance containing proteins or polypeptides or, optionally, carbohydrates possessing a specific ability to bind vitamin $B_{12}$. A well known example of such a substance is intrinsic factor, a muco protein from the ventriculus mucous membrane. Another example is a protein fraction from blood plasma which is capable of binding vitamin $B_{12}$.

The invention is based on the discovery that substances, e.g. intrinsic factor, exist which are capable of specifically binding vitamin $B_{12}$ and that this binding takes place irrespective of whether vitamin $B_{12}$ is labelled with a radiosotope or not. The binding of labelled and unlabelled vitamin $B_{12}$ to the substance capable of binding vitamin $B_{12}$, e.g. intrinsic factor, takes place in proportion to the concentration of labelled and unlabelled vitamin $B_{12}$, respectively.

The major advantage presented by the present method is that the substance capable of binding vitamin $B_{12}$ is not in solution but is very securely bound to an insoluble carrier and thus the labelled vitamin $B_{12}$, which in the determination reacts with and is bound to the substance capable of binding vitamin $B_{12}$, can be readily separated from the unbound, labelled vitamin $B_{12}$ by, for instance, a simple centrifugation or filtration. The test is easily performable as known quantities of particles with the substance capable of binding vitamin $B_{12}$ attached thereto can be dispensed before hand in, for instance, test tubes, and may be stored without losing their binding property. The total procedure, including the separation of the free labelled vitamin $B_{12}$ and the bound labelled vitamin $B_{12}$ can be effected in one and the same test tube without any extra additions of precipitating agents or the like.

The labelling of vitamin $B_{12}$ with a radioisotope can be effected in a conventional manner, a suitable isotope for the purpose being selected. A radioisotope of cobalt is particularly suitable for the purpose. Vitamin $B_{12}$ labelled with a cobalt radiosiotope is accessible commercially and many hospital laboratories are now equipped to measure this isotope.

Particles of water-insoluble polymers are used as the carrier of the substance capable of binding vitamin $B_{12}$. The polymer is selected so that it contains or can be provided with suitable reactive groups, e.g. amino groups, hydroxyl groups and carboxyl groups, to make possible binding of the substance capable of binding vitamin $B_{12}$, e.g. intrinsic factor, to the polymer by bridges with bonds of covalent character.

It is particularly suitable to select polymer particles comprising a three-dimensional network, held together by covalent bonds. Such particles, even if they are capable of swelling in water, are completely insoluble therein and can therefore not release any of the polymer material or the substance bound thereto by covalent bonds, e.g. during washing procedures. Examples of such polymer particles are grains of polymers obtained by cross linking substances containing a plurality of hydroxyl groups, such as carbohydrates and sugar alcohols, e.g. dextran, starch, dextrins and other polysaccharides and polyvinyl alcohol with a bifunctional substance, e.g. bifunctional substances of the type X–R–Z, wherein, for instance, X and Z are each halogen or an epoxy group and R the residue of the bifunctional substance, e.g. an aliphatic radical containing from 3 to 10 inclusive carbon atoms.

For this purpose grains of the commercially accessible product Sephadex can be used, for instance; this product containing dextran cross linked with glycerine etherbridges, obtained by treating dextran with epichlorohydrin. Sephhadex and products obtained in a similar manner are capable of swelling in water but are insoluble gel grains. They contain hydroxyl groups and can thereby be easily substituted by other groups e.g. such as those containing amino groups or carboxyl groups, and are well suited for producing bridges, by covalent linkages, to the substance capable of binding vitamin $B_{12}$, e.g. intrinsic factor.

Other examples are reactive derivatives obtained by treating a copolymer of dextran with epichlorohydrin (Sephadex) with cyanogen halides such as cyanogen bromide. Such reactive derivatives will readily react with intrinsic factor.

Small particles are preferably selected so that a larger contact surface is obtained.

The substance capable of binding vitamin $B_{12}$ is bound to these carrier particles, by covalent bonds, under conditions which are so mild that its reactivity is not reduced to any appreciable extent. Because of the covalent bonds the substance capable of binding vitamin $B_{12}$ cannot be loosened and washed out from the particles. Used for chemically binding the substance capable of binding vitamin $B_{12}$ to the polymer particle are reactive groups contained in this polymer such as amino groups, hydroxyl groups and carboxyl groups, a bridge having covalent bonds being established between the substance capable of binding vitamin $B_{12}$ (P) and the polymer particle e.g. of the type:

P–NH.CS.NH–Polymer particle

P+NH.CO.NH+Polymer particle

P–N=N–Polymer particle

The bridge established between the substance capable of binding vitamin $B_{12}$, e.g. intrinsic factor, and the polymer need not be determined as to its structure and permits a great variation in its selection because the purpose thereof is only to prevent the substance capable of binding vitamin $B_{12}$ from being washed out.

During the analysis operation a solution of vitamin $B_{12}$ of known concentration is suitably used as a standard.

The radioactivity determination can be effected by known methods, e.g. with the assistance of scintillation detectors.

The quantity of particles having the substance capable of binding vitamin $B_{12}$ attached thereto is selected, inter alia, with consideration to the degree of sensitivity required for the test.

The quantity of labelled vitamin $B_{12}$ added for the reaction is selected, for instance, so that about 40–60% of the labelled vitamin $B_{12}$ is bound to the substance capable of binding vitamin $B_{12}$, when no competing unlabelled vitamin $B_{12}$ is present. The incubation may be effected at different temperatures but is preferably carried out at temperatures between +4 and 25° C. It is not necessary to continue the reaction between vitamin $B_{12}$ and the substance capable of binding vitamin $B_{12}$ to completion. The incubation is interrupted after, for instance, two hours, but may also be interrupted later, e.g. after 24 hours. It is important that the reaction time and temperature are selected equal for sample solutions and standard solutions.

In that the method is simple, rapid, practical and gives accurate analysis results it is well suited for quantitative determinations, even for routine work, and permits the determination of very small amounts of sample substance.

The method determines free vitamin $B_{12}$. In serum, for instance, vitamin $B_{12}$ is bound to a protein. Thus, in the determination vitamin $B_{12}$ is released before the determination, e.g. by heating with hydrochloric acid.

Excess of protein capable of binding vitamin $B_{12}$ in serum, for instance, may also be determined by means of the present method, in that particles having a substance capable of binding vitamin $B_{12}$ attached thereto and suitable amounts of labelled vitamin $B_{12}$ are added to untreated serum whereafter, subsequent to the particles having been separated, the radio-activity is measured.

The invention also includes a reagent for use in the determination of vitamin $B_{12}$. This reagent contains particles of water insoluble polymers to which have been bound, by covalent bounds, a substance capable of binding vitamin $B_{12}$, in dried, e.g. lyophilized form.

According to an embodiment of the invention such a reagent may be contained in a sealed ampoule.

The invention also includes a test pack for the determination of vitamin $B_{12}$ chiefly comprising one or more sealed ampoules containing particles of water insoluble polymers to which have been bound, by covalent bonds, a substance capable of binding vitamin $B_{12}$ in dried, e.g. lyophilized, form and one or more ampoules wth vitamin $B_{12}$ labelled wth a radioisotope in dried, e.g. lyophilized form.

The invention will be further illustrated in the following by means of detailed examples concerning the determination of vitamin $B_{12}$ in blood serum.

EXAMPLE 1

Determination of vitamin $B_{12}$ in blood serum (A) Preparation of particles having a substance capable of binding vitamin $B_{12}$ attached by covalent bonds. —Finely grained particles of the product Sephadex (G25, superfine) were used as a starting material, the product being dextran cross linked with glycerine ether-bridges and substituted with p-nitrophenoxy-hydroxy-propyl-ether groups to a substitution degree of 200 μmol of nitro groups per gam of dry substance, 10 g. of the substituted Sephadex product was introduced together with 50 ml. water into a two-necked flask, whereafter the temperature of the mixture was maintained at 35° C. The mixture was agitated and at the same time 25 ml. of a 5 N aqueous solution of sodium hydroxide and 6 g. of sodium dithionite were added, for reducing the nitro groups into amino groups. After approximately 30 mins. further 5 g. of sodium dithionite were added. The reduction process was interrupted after about one hour whereafter neutralization took place with dilute hydrochloric acid, the solid substance being removed by filtration and washed with distilled water on a suction filter.

10 g. of the above obtained Sephadex product substituted wth p-amino-phenoxy-hydroxy-propyl groups were introduced into a reaction flask together with 100 ml. of a 10 percent solution of thiophosgene in carbon tetrachloride. The flask was sealed with a plug and the mixture agitated for about two hours. The obtained mixture was cooled in an ice bath, whereafter the flask was opened and the contents removed by filtration. The residue of filtration was washed with a 0.1 M aqueous solution of sodium hydrogen carbonate, distilled water and acetone. The residue was then dried in a drying oven at 60–80° C.

2 grams of the Sephadex product obtained according to the above substituted with a p-isothio-cyanato-phenoxy-hydroxyl-propyl groups were swollen in 6 ml. of a 0.1 M aqueous solution of sodium hydrogen carbonate The agitator was connected, whereafter 4 ml. of the same sodium hydrogen carbonate solution containing 95 mg. of intrinsic factor were added in a dropwise manner. The mixture was agitated for 24 hours at 20° C., and then filtered. The residue of filtration was washed with a 0.5 M aqueous solution of sodium hydrogen carbonate to remove unreacted substances The product can be dried carefully e.g. by lyophilization.

(B) Determination.—The analyses are suitably effected in glass or plastic tubes of 50 × 10 mm. in dimension. A 0.05 M tris-buffer with pH 7.4 containing 0.9% of NaCl, 0.1% of bovine serum albumin and 0.01% of sodium azide was used as a diluent. Prior to the analysis the vitamin $B_{12}$ in the serum was separated from serum protein by heating with hydrochloric acid in the following manner: 0.5 ml. of serum +0.5 ml. of a 0.9% percent solution of NaCl added with 2 micro grams of NaCN per ml. + 1 ml. of 0.1 N HCl were placed in a boiling water bath for 20 minutes, whereafter the solution was cooled with running cold water.

The determination is then carried out according to the following, for instance:

(1) 0.25 ml. of serum solution treated according to the above is introduced into each of two tubes.

(2) 0.25 ml. of standard solutions of different concentrations of vitamin $B_{12}$, e.g. 1000, 400, 100, 40, 10 and 0 pg./ml. diluted in the aforesaid buffer with addition of two micro grams of NaCl per ml. are each introduced into two tubes.

(3) 0.1 ml. of a solution containing 1 nanogram of vitamin $B_{12}$ labelled with $^{58}Co$ per ml. diluted in buffer with an addition of two μg. NaCN per ml. is added to all tubes.

(4) 1 ml. of a homogenized suspension of the polymer particles (1 mg. per ml.) to which intrinsic factor has been bound by covalent bonds is added to each of all tubes.

(5) Incubation for 3 hours at room temperature or 4° C., the tubes being slowly rotated.

(6) The particles are centrifuged down at 3000 r.p.m. for 5 minutes.

(7) The particles are washed twice with a 0.9 percent solution of NaCl. Subsequent to the last removal by suction of the supernatant the tubes are placed in counter tubes for estimating the radiation from the bound labelled vitamin $B_{12}$.

(8) The number of "counts" for a certain time from the standard tubes is set on a "counts-dose" diagram on lin-log scale, from which the amount of vitamin $B_{12}$ in the unknown samples can later be calculated.

Alternatively, subsequent to centrifuging in item 6 above one ml. of the supernatant is transferred in counter tubes, whereafter the radiation from free labelled vitamin $B_{12}$ can be estimated. "Counts" from the standard tubes can be entered in the same way into a count-dose diagram in lin-log scale and the amount of vitamin $B_{12}$ in the unknown test samples can then be estimated graphically in the same way as above.

EXAMPLE 2

Determination of vitamin $B_{12}$ in an aqueous sample (A) Preparation of particles having a substance capable of binding vitamin $B_{12}$ attached thereto by covalent bonds.—10 grams of a copolymer obtained by reacting dextran with epichlorohydrin (Sephadix G25, superfine) were swollen, with agitation for 3 min., in 200 ml. of a solution of cyanogen bromide, containing 10 grams of the latter per 100 ml. of water. There were then added an aqueous 5 M solution of sodium hydroxide with agitation to a pH-value of 10.7. This value was maintained constant for 8 minutes. The temperature was maintained at 20° C. in the whole procedure. The mixture was then transferred to a glass filter and washed carefully with water to neutral reaction. The particles separated off were shrunk by washing with acetone. The particles were dried carefully and could be stored at, e.g., −20° C.

2 grams of the obtained particles activated with cyanogen bromide were swollen in 6 ml. of an aqueous 0.1 M solution of sodium hydrogen carbonate. The stirrer was switched on after which 4 ml. of the same solution of sodium hydrogen carbonate, containing 100 mg. of intrinsic factor, were added in a drop-wise manner. The mixture was agitated for 24 hours after which filtration took place. The residue of filtration was washed with an aqueous 0.5 M solution of sodium hydrogen carbonate to remove unreacted substances. The product could be dried carefully, e.g., by lyophilization.

(B) Determination.—This procedure was carried out in a manner similar to Example 1(B).

What we claim is:

1. A method for determining vitamin $B_{12}$ in an aqueous sample, which comprises contacting particles of water-insoluble polymers to which a substance capable of binding vitamin $B_{12}$ has been bound, by covalent bonds, with the sample and with a certain amount of vitamin $B_{12}$ labeled with a radioisotope, and subsequent to the reaction between vitamin $B_{12}$ and the substance capable of binding vitamin $B_{12}$ attached to the particles having taken place, separating the particles from the sample liquid and determining the radioactivity of the particle material.

2. A method according to claim 1, wherein the radioactivity is also determined in the fluid.

3. A method according to claim 1, wherein vitamin $B_{12}$ labelled with a radioisotope of cobalt is used in the determination.

4. A method according to claim 1, wherein the substance capable of binding vitamin $B_{12}$ which has been bound to the polymer particles by covalent bonds, is intrinsic factor.

5. A method according to claim 1, wherein the determination is effected quantitively.

6. A method for determining vitamin $B_{12}$ in an aqueous sample, which comprises contacting particles of water-insoluble polymers to which a substance capable of binding vitamin $B_{12}$ has been bound, by covalent bonds, with the sample and with a certain amount of vitamin $B_{12}$ labelled with a radioisotope, and subsequent to the reaction between vitamin $B_{12}$ and the substance capable of binding vitamin $B_{12}$ attached to the particles having taken place, separating the particles from the sample liquid and determining the radioactivity in the fluid.

7. A method according to claim 6, wherein vitamin $B_{12}$ labelled wih a radioisotope of cobalt is used in the determination.

8. A method according to claim 6, wherein the substance capable of binding vitamin $B_{12}$ which has been bound to the polymer particles by covalent bonds, is intrinsic factor.

9. A method according to claim 6, wherein the determination is effected quantitively.

10. A reagent for use in the determination of vitamin $B_{12}$, containing particles of water insoluble polymers to which have been bound, by covalent bonds, a substance capable of binding vitamin $B_{12}$, in dried form.

11. A reagent according to claim 10, wherein the reagent is in lyophilized form.

12. Sealed ampoules containing the reagent as claimed in claim 11.

13. Test pack for the determination of vitamin $B_{12}$ chiefly comprising one or more sealed ampoules containing particles of water insoluble polymers to which have been bound, by covalent bonds, a substance capable of binding vitamin $B_{12}$ in dried form and another ampoule with vitamin $B_{12}$ labelled with a radioisotope in dried form.

14. Test pack according to claim 13, wherein the particles of water-insoluble polymers to which have been bound by covalent bonds a substance capable of binding vitamin $B_{12}$ is in lyophilized form.

15. Test pack according to claim 14, wherein the vitamin $B_{12}$ labelled with a radioisotope is in lyophilized form.

*16. A method according to claim 1, wherein the substance capable of binding vitamin $B_{12}$ is a protein fraction from blood plasma.*

*17. A method according to claim 1, wherein said covalent bonds are formed through a group of the formula —NH·CS·NH—, —NH·CO·NH—, or —N=N—.*

*18. A method according to claim 17, wherein said group is —NH·CS·NH—.*

*19. A method according to claim 1, wherein said water-insoluble polymers contain at least one reactive group selected from the group consisting of amino, hydroxyl and carboxyl.*

*20. A method according to claim 19, wherein said reactive group is hydroxyl and wherein said substance capable of binding vitamin $B_{12}$ is covalently bound to said polymer through reaction with a cyanogen halide.*

*21. A method according to claim 19, wherein said reactive group is amino and wherein said substance capable of binding vitamin $B_{12}$ is covalently bound to said polymer through reaction with a cyanogen halide.*

*22. A method according to claim 1, wherein said polymer is obtained by cross-linking a material selected from the group consisting of carbohydrates, sugar alcohols, and polyvinyl alcohol, with a bifunctional compound of the formula X—R—Z, wherein X and Z are each independently halogen or epoxy, and R is an aliphatic radical containing from 3 to 10 carbon atoms.*

*23. A method according to claim 22, wherein said material is dextran and said bifunctional compound is epichlorohydrin.*

*24. A reagent according to claim 10, wherein the substance capable of binding vitamin $B_{12}$ is a protein fraction from blood plasma.*

*25. A reagent according to claim 10, wherein the substance capable of binding vitamin $B_{12}$ is intrinsic factor.*

*26. A reagent according to claim 10, wherein said covalent bonds are formed through a group of the formula —NH·CS·NH—, —NH·CO·NH—, or —N=N—.*

*27. A reagent according to claim 26, wherein said group is —NH·CS·NH—.*

*28. A reagent according to claim 10, wherein said water-insoluble polymers contain at least one reactive group selected from the group consisting of amino, hyroxyl and carboxyl.*

*29. A reagent according to claim 28, wherein said reactive group is hydroxyl and wherein said substance capable of binding vitamin $B_{12}$ is covalently bound to said polymer through reaction with a cyanogen halide.*

*30. A reagent according to claim 10, wherein said polymer is obtained by cross-linking a material selected from the group consisting of carbohydrates, sugar alcohols, and polyvinyl alcohol, with a bifunctional compound of the formula X—R—Z, wherein X and Z are each independently halogen or epoxy, and R is an aliphatic radical containing from 3 to 10 carbon atoms.*

*31. A reagent according to claim 30, wherein said material is dextran and said bifunctional compound is epichlorohydrin.*

* * * * *

UNITED STATES PATENT OFFICE

CERTIFICATE OF CORRECTION

Patent No. Re.29,480 Dated November 11, 1976

Inventor(s) Rolf Axen et al

It is certified that error appears in the above-identified patent and that said Letters Patent are hereby corrected as shown below:

Column 1, line 40: "radiosotope" should read -- radioisotope --.

Column 2, line 31: "Sephhadex" should read -- Sephadex --; line 61: "P + NH.CO.NH + Polymer particle" should read -- P - NH.CO.NH - Polymer particle.

Column 3, line 44: "bounds" should read -- bonds --.

Column 4, line 1: "per gam" should read -- per gram --; lines 29-30: "with a" should read -- with --; "oxy-hydroxyl-propyl" should read -- oxy-hydroxy-propyl --.

Signed and Sealed this

*Twenty-third* Day of *May 1978*

[SEAL]

*Attest:*

RUTH C. MASON
*Attesting Officer*

LUTRELLE F. PARKER
*Acting Commissioner of Patents and Trademarks*